United States Patent [19]
Funke et al.

[11] 4,284,082
[45] Aug. 18, 1981

[54] VENTRICULAR SYNCHRONIZED ATRIAL PACEMAKER AND METHOD OF OPERATION

[75] Inventors: Hermann D. Funke, Bonn, Fed. Rep. of Germany; Lodewijk-Jozef Herpers, Kerkrade-West, Netherlands

[73] Assignee: Medtronic B.V.Kerkrade, Kerkrade-West, Netherlands

[21] Appl. No.: 102,684

[22] Filed: Dec. 12, 1979

[51] Int. Cl.³ .............................................. A61N 1/36
[52] U.S. Cl. ............................................ 128/419 PG
[58] Field of Search ................................ 128/419 PG

[56] References Cited
U.S. PATENT DOCUMENTS

| | | | |
|---|---|---|---|
| 3,557,796 | 1/1971 | Keller, Jr. et al. | 128/419 PG |
| 3,747,604 | 7/1973 | Berkovits | 128/419 PG |
| 3,783,878 | 1/1974 | Thaler et al. | 128/419 PG |

*Primary Examiner*—William E. Kamm
*Attorney, Agent, or Firm*—Joseph F. Breimayer; Lew Schwartz; Robert C. Beck

[57] ABSTRACT

An atrial pacemaker having an atrial pacing rate adjusted to correspond to a detected ventricular heart rate to maintain A-V synchrony in a range between a minimum and maximum pacing rate. Sensed ventricular depolarizations not associated with a preceding atrial pacing stimulus cause the atrial pacing rate to be increased. When A-V synchrony is restored at a higher rate, the rate is decreased. Underdrive stimulation to treat pathologic tachycardia is achieved as the atrial pacing rate is increased in steps to the maximum pacing rate, normally lower than typical tachycardia rates.

25 Claims, 3 Drawing Figures

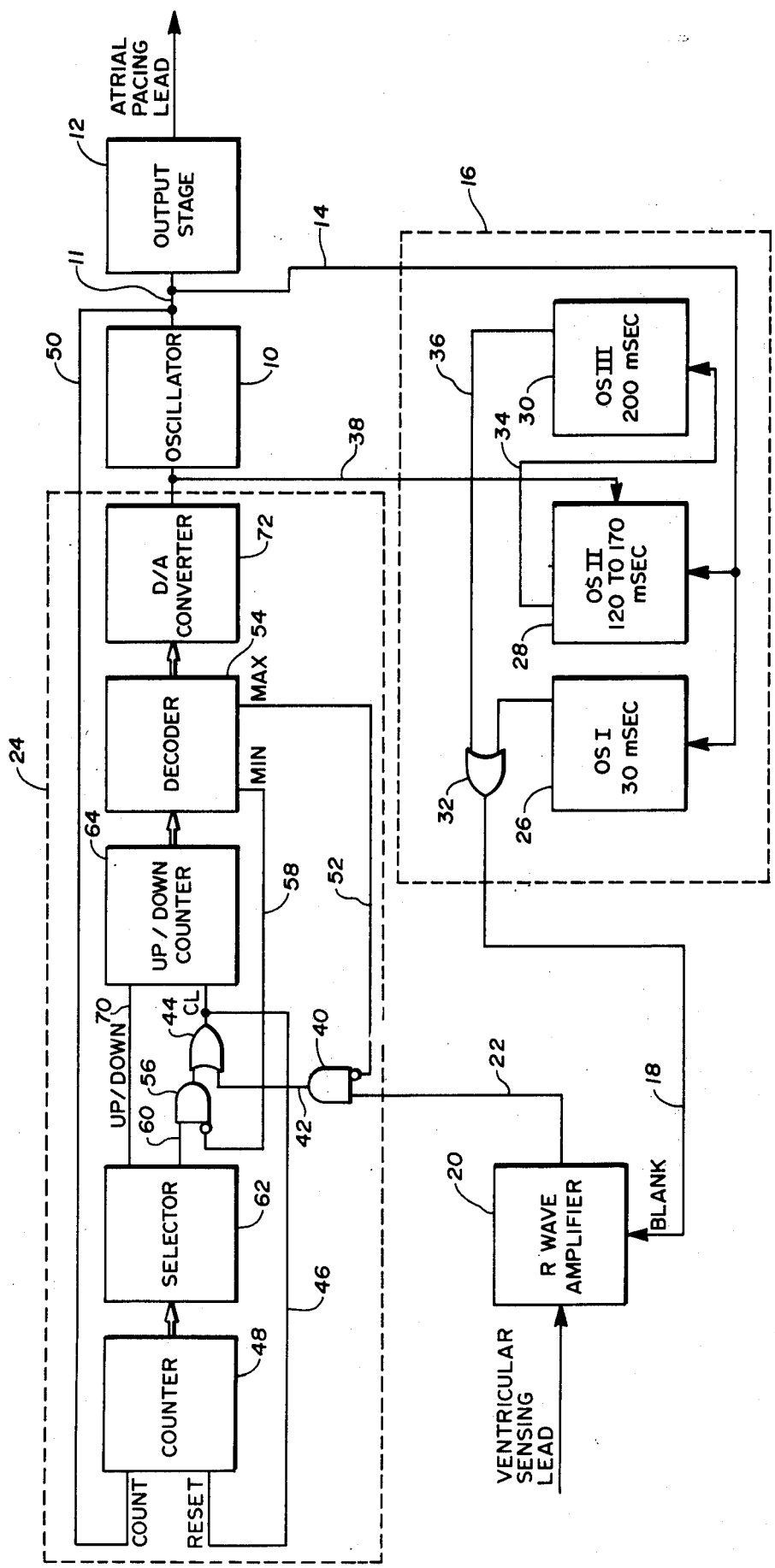

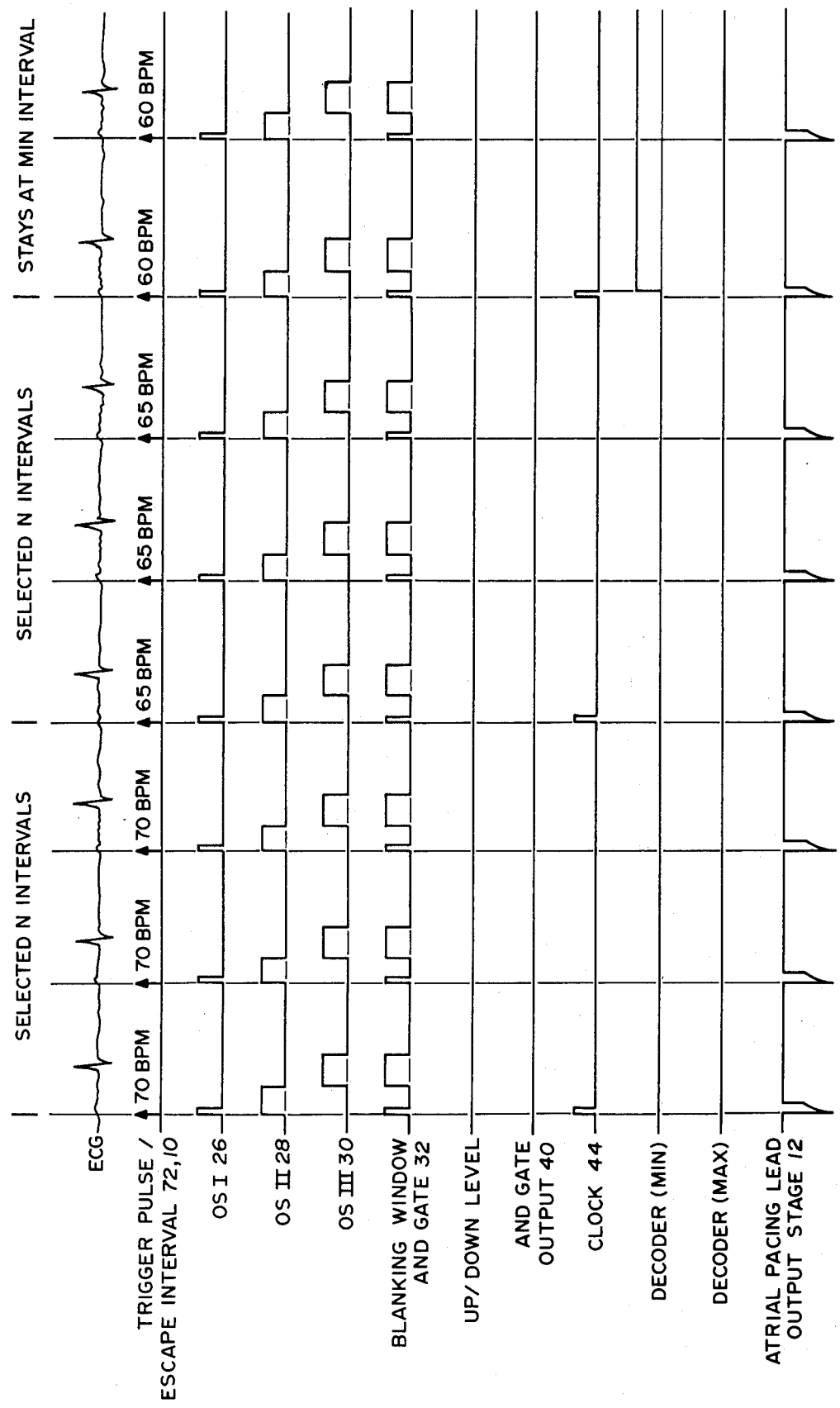

VENTRICULAR SYNCHRONIZED ATRIAL PACEMAKER AND METHOD OF OPERATION

BACKGROUND OF THE INVENTION

1. Field of the Invention

This invention relates to artificial cardiac pacemakers, either external or implantable having an atrial pulse generator, the stimulating frequency of which is controlled by the sensing of ventricular events.

2. Description of the Prior Art

The implantable cardiac pacemaker, shown in U.S. Pat. No. 3,057,356 and subsequent patents permits innocuous, painless, long-term cardiac stimulation at low power levels by utilizing a small completely implanted transistorized and battery operated pulse generator connected via a flexible lead bearing an electrode directly in contact with cardiac tissue. Most pulse generators consist of a stimulating circuit and a sensing circuit both of which draw current from the battery. In the presence of complete heart block, an asynchronous pulse generator with only a stimulating circuit may be used, however, in most instances, noncompetitive triggered or inhibited pulse generators having the sensing circuit are preferred and dominate the pacemaker market. The demand, synchronous or triggered pulse generators are especially useful in patients with spontaneous cardiac activity because of their ability to sense intrinsic cardiac rhythm (atrial or ventricular depending on variety and electrode position), and to alter the pacemaker output accordingly. Such pacemakers are shown for example, in U.S. Pat. Nos. 3,253,596 (P-wave synchronous), 3,478,746 (ventricular inhibited) and are described in the pacing literature.

More recently, attention has been paid to the physiological aspects of cardiac pacing therapy and particularly to pacing systems for maintaining synchronous atrial and ventricular depolarization of the heart. In early atrial synchronized (or A-V synchronous) pacing, atrial depolarization is sensed through one electrode, and after an appropriate delay the ventricle is paced through a different electrode, thereby restoring the normal sequence of atrial and ventricular contraction and allowing the pacer to respond to physiologic needs by increasing its rate. Below a predetermined minimal atrial rate, however, the pacemaker reverts to its basic ventricular pacing rate. In atrial synchronous ventricular inhibited pacers of the type described in U.S. Pat. Nos. 4,059,116 and 3,648,707, the ventricular depolarizations are also sensed and inhibit or reset the timing of the ventricular stimulating pulse generator.

A more complex method of restoring synchrony is by the atrial ventricular sequential pacing of the type described in U.S. Pat. Nos. 3,595,242 and subsequent patents which possess atrial and ventricular pulse generators and associated electrodes and a ventricular sensing circuit. In atrial ventricular sequential pacing, the atria and ventricles are paced in proper sequence, the atrial and ventricular pulse generator timing circuits being reset on sensing spontaneous ventricular activity.

Finally, copending U.S. patent application Ser. No. 940,694 filed Sept. 8, 1978, now abandoned for continuation application, Ser. No. 120,237 filed Feb. 11, 1980, and assigned to the assignee of the present invention, discloses a pacemaker which, if required, may stimulate the atrium and/or ventricle on demand and which is able to maintain synchrony as the sensed atrial rate increases. A pacemaker of this type is capable of distinguishing between bradycardia and normal heart function and to provide atrial and/or ventricular pacing in the following modes: inhibited in the case where the atrium and ventricle beat at a sufficient rate; atrial demand in instances where the atrium is beating at an insufficient rate and must be stimulated whereas the ventricle properly follows; atrial synchronous when the atrium depolarizes at a sufficient rate but the ventricle does not follow within a prescribed A-V interval; and dual demand when neither the atrium and the ventricle spontaneously depolarize at the desired rate.

In all of the pacemakers of the types described above where an atrial stimulation is provided, the atrial pulse generator posseses a timing circuit having a predetermined escape interval. The timing circuit may be reset in certain instances by sensing of a ventricular and/or atrial depolarization detected prior to the timing out of the escape interval. In recent versions, the atrial (and ventricular) escape interval may be remotely programmed to provide a number of basic pacing rates extending batween a MINIMUM and MAXIMUM possible rate. Thus, if the natural atrial rate exceeds the basic interval of the atrial pulse generator timing circuit, the atrial pulse generator will be inhibited. Similarly, if the sensed ventricular depolarizations occur at a rate exceeding the basic rate of the atrial pulse generator timing circuit, then it again will be inhibited. In the former case, no physiological harm is done, since the heart is beating at a rate that is within the MAXIMUM and MINIMUM desired rate. In the latter case, however, if the ventricle of the heart is beating at a rate exceeding the atrial and ventricular escape intervals, the atrium is not depolarizing in synchrony with the ventricle and the hemodynamically desirable synchronism is lost. The patient may then suffer a loss of cardiac output at a time when the patient's physiology is demanding an increased cardiac output. That is, when the ventricle is contracting at a rate exceeding the atrium, it indicates that the patient is undergoing some stress or exercise that requires a greater cardiac output.

For example, if a patient has an absolute sinus bradycardia (that is, is devoid of an underlying atrial heart rhythm), then if an increasing load is applied to the patient's heart, the heart rate of the ventricle may increase to a rate exceeding the preset rate of the atrial pulse generator timing thereby inhibiting atrial stimulation. The atrium, no longer pumps in synchrony with the ventricle and the patient loses the atrial contribution to cardiac output. Thus, in a time of need, the patient may suffer cardiac insufficiency.

In other patients the sinus rhythm may become irregular as the load on the heart is increased through exercise, and the atrial ventricular synchrony again becomes disturbed. In such cases, it would be desirable to maintain the atrial ventricular synchrony at rates in excess of the preset atrial and ventricular rates of the pacemaker.

Similarly, it would be desirable to reestablish atrial and ventricular synchrony in instances where ventricular extrasystoles manifest themselves at irregular intervals. In the prior art pacemakers the extrasystole is sensed and inhibits both the atrial and ventricular pulse generators until a newly established escape interval times out. In such instances, the atrial and ventricular synchronism is lost and the heartbeat is erratic. It would be desirable to pace the heart in such a manner as to restore normal cardiac output as quickly as possible on the occurence of an extrasystole.

In addition it would be desirable to recognize and treat tachycardia. In conventional tachycardia detection pacemakers, tachycardia is detected by sampling the ventricular rate, and be it a physiologic or a pathologic tachycardia, the fixed limit of e.g. 150 BPM provokes interruption measures of the tachycardia breaking pacemaker. However, in a given patient, the high heart rate does not necessarily indicate whether a pathologic tachycardia is present; it might be as well a normal frequency as a response to exercise. Hence, conventional tachycardia breaking pacemakers would try to break this fast sinus rhythm, and this clearly would be dangerous, as a normal sinus tachycardia cannot be broken, but a lot of extra cardiac activity would be produced. In the same patient, a frequency of 120 could mean a pathologic (reentry-) tachycardia lending itself to interruption, whereas a frequency of 150 BPM in the same patient could be a physiologic tachycardia. This means, that the actual frequency of the heart is a bad indicator of tachycardia to be interrupted.

Conventional treatment calls for sensing such arrythmia rates in the ventricle and pacing the ventricle at higher (overdrive), lower (underdrive) or variable pacing rates for a period of time.

Such pacemakers may not be able to distinguish a single PVC from the first tachyarrythmia beat and may go into the tachycardia treatment mode unnecessarily.

SUMMARY OF THE INVENTION

Accordingly, in recognition of the above stated disadvantages in the prior art pacemakers, the present invention provides an artificial cardiac pacemaker which in response to ventricular electrical activity or depolarization not accompanied by a naturally occurring preceding atrial electrical activity or depolarization, causes the atrial escape interval of the atrial pulse generator timing circuit to be decreased by a predetermined interval, thus increasing the pacing rate. That is, on sensing such a ventricular depolarization, the atrial timing circuit escape interval is shortened a predetermined amount to cause atrial stimulation pulses to be provided at a rate exceeding the preceding rate by a predetermined value. If a ventricular depolarization is again sensed at a time prior to the provision of the atrial stimulation pulse, then the atrial escape interval is again foreshortened a predetermined amount until, ultimately, the atrial escape interval is shorter than the natural ventricular escape interval and atrial pulses precede ventricular depolarizations, resulting in the restoration of atrial and ventricular synchrony.

Stated in another manner, the invention involves a method and apparatus of synchronous heart pacing which follows the steps of generating atrial pacing stimulating pulses adapted to be applied to the atrium at an atrial pacing rate; sensing ventricular heart depolarizations; and adjusting the atrial pacing rate when the ventricular depolarizations do not fall within a predetermined atrial-ventricular (A-V) delay interval following an atrial pacing pulse.

The atrial pacing rate is adjusted by increasing it when ventricular depolarizations are sensed before or after the predetermined A-V delay interval. The atrial pacing rate increases to a maximum rate and returns to its minimum rate when synchrony is restored, that is, when the ventricular depolarizations fall into the A-V delay interval.

In the preferred embodiment of our invention, the pacemaker circuitry includes timing and rate adjusting circuitry for causing the atrial escape interval to be foreshortened a predetermined amount for a predetermined number of atrial output pulses. The timing and rate adjusting circuitry includes blanking window means for timing the interval between the atrial stimulation pulses and the ventricular depolarizations. As the time interval grows shorter indicating that the ventricular depolarization rate is about to exceed the atrial pacing rate, the logic circuit means steps up the rate of the atrial pulse generator. After a predetermined number of atrial stimulation pulses, the logic circuit means provides for a reduction by a predetermined amount in the atrial pacing rate. The atrial pacing rate is thus decreased in steps until the preset or programmed MINIMUM rate is reached.

Furthermore, the atrial simulation rate may be increased from the preset or programmed rate of the pacemaker to the upper rate limit or MAXIMUM rate of the pacemaker. As the upper rate limit is approached, the blanking window is automatically foreshortened by a predetermined amount, since it is likely that naturally following ventricular depolarization will, at higher rates, follow more closely the atrial depolarization.

Advantageously to the patient, the artificial cardiac pacemaker and the method of pacing of our invention maintains the desirable atrial ventricular synchrony in instances where the prior art pacemakers would revert to a standby or inhibited mode. Thus, the patient enjoys the full cardiac output of his heart when it is needed the most up to a safe upper rate limit.

The ventricular synchronous atrial pacing apparatus and method described above has the additional advantage of responding to both physiologic tachycardia and to sudden, pathologic (reentry) tachycardia. When a sudden tachycardia occurs, the atrial rate is increased, but only by a fixed amount. The atrial pacing rate may still be less than the tachycardia rate and hence, neither will be in synchrony. As the atrial pulse rate continues to increase it will pace in an underdrive mode with varying (shortening) escape intervals. At some point, the atrial pacing pulse may be applied in the vulnerable cycle and may break the tachycardia. Then the rate of the atrial pulse generators will stabilize and slowly decrease, in the manner to be described, allowing the heart itself to slowly stabilize without a sudden decrease in its rate.

The foregoing and additional advantages and characterizing features of the present invention will become clearly apparent upon reading of the ensuing detailed description of an illustrative embodiment thereof together with the included drawings depicting this theme.

BRIEF DESCRIPTION OF THE DRAWINGS

FIG. 1 is a block diagram illustrating the preferred embodiment of the artificial pacer of the present invention; and FIGS. 2a and 2b illustrate the signals sensed by or developed at various points in the block diagram of FIG. 1 during modes of operation of the preferred embodiment of our invention.

DETAILED DESCRIPTION OF THE PREFERRED EMBODIMENT

Figure 2A:
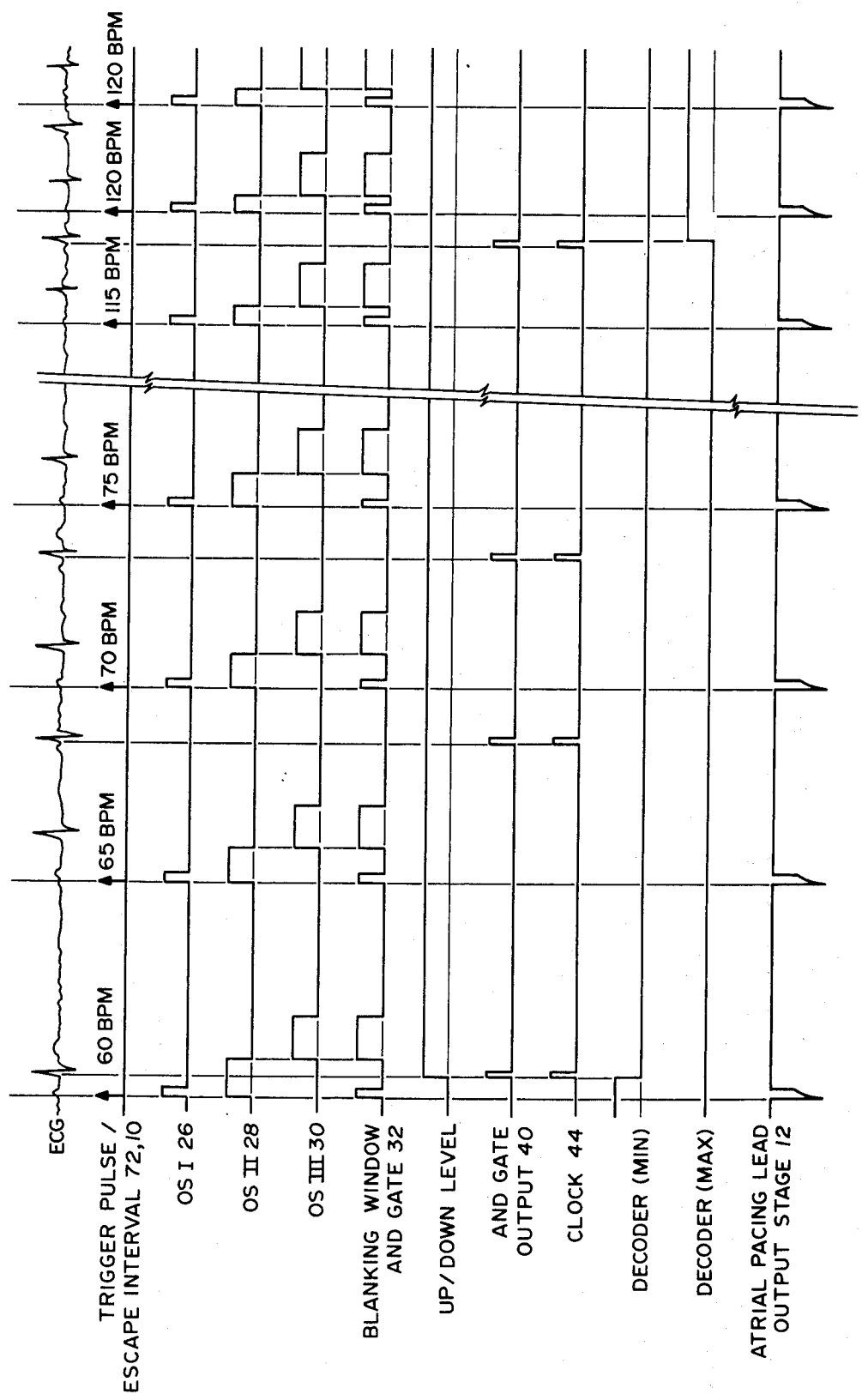

Referring now to FIG. 1 there is shown the atrial pacing and ventricular sensing portion of an artificial cardiac pacemaker pulse generator circuit constructed in accordance with the present invention. The circuit is adapted to receive ventricular heart signals from a ventricular sensing lead and generate atrial pacing pulses applied to an atrial pacing lead neither of which is shown explicitly in FIG. 1. The circuit may either be constructed into a pacemaker pulse generator having the components depicted for treatment of the specific disorder of sinus bradycardia of the type treated ordinarily by atrial demand pacemakers. Alternatively, the circuit may be incorporated into the atrial ventricular sequential pacemakers or dual demand pacemakers described earlier. In the latter case, certain of the components, including oscillators, output stages and sensing amplifiers may already be present in the circuitry of such pacemakers.

Turning more particularly to FIG. 1, there is shown an oscillator 10 conventionally found in pacemakers which includes timing means for establishing an atrial escape interval of the pacemaker. The oscillator 10 has an output terminal which is connected via conductor 11 to the input of the output stage 12 which again is ordinarily found in pacemakers of the type described previously. The output stage 12 is coupled to an atrial pacing lead and, on being triggered by a trigger pulse generator by the oscillator 10, generates the atrial pacing pulse. In the absence of any disturbing factor, the oscillator 10, output stage 12, and atrial pacing lead comprise the elements of an asynchronous atrial pacemaker. The oscillator 10 continually times out and provides a trigger pulse to the output stage 12 which applies a stimulating pulse of a preset magnitude and duration to the atrial pacing lead to stimulate the heart at the rate established by the timing circuit in oscillator 10. Although not shown on this drawing it will be understood that the components of the circuit are powered by an appropriate power source, the oscillator 10 may be reset by sensed atrial or ventricular depolarizations of the heart recurring at a rate exceeding the rate of the timing circuit, the timing circuit may be remotely programmable to establish any number of basic pacing rates and escape intervals, and the oscillator 10 may possess an upper rate limit circuit which limits the rate at which it is capable of producing trigger pulses to an upper safe limit. Such circuitry is shown, for example, in copending U.S. Pat. application Ser. No. 958,328 filed Nov. 6, 1978, now abandoned, and assigned to the assignee of the present invention.

Returning now to the remaining circuit components depicted in the block diagram of FIG. 1, the trigger pulse output of oscillator 10 is also coupled via conductor 14 and timing window generator 16 and conductor 18 to the blanking input of R-wave sense amplifier 20. The R-wave or ventricular sense amplifier 20 is adapted to be coupled to a ventricular sensing lead (not shown) and may take the form of a conventional sense amplifier of the type shown in U.S. Pat. No. 4,059,116 and assigned to the assignee of the present invention. The output of the R-wave amplifier is coupled through lead 22 to the rate controlling circuit 24. The elements 16 and 24, depending on the timing of the atrial escape interval established by oscillator 10 and R-waves sensed by the R-wave amplifier 20, maintain the atrial-ventricular synchrony in instances where the sensed ventricular depolarizations occur at a rate exceeding the atrial escape interval of oscillator 10.

The timing window generator 16 comprises first, second and third one-shot circuits 26, 28 and 30 and OR gate 32. The trigger signal generated by the oscillator 10 is applied through conductor 14 to the first and second one-shot circuits 26 and 28. One-shot 26 is set by the trigger pulse for a relatively short interval, such as 10–30 milliseconds, which is coupled through OR gate 32 and conductor 18 to the blank input of R-wave amplifier 7 to cause the amplifier to be blank for the set interval of one-shot 26. R-wave amplifier 20 is thus blanked for a short interval commencing upon the generation of a trigger pulse for the duration of the stimulating output pulse produced by output stage 12. This prevents the R-wave amplifier 20 from sensing the stimulus provided by the atrial pulse generator.

The trigger pulse is also applied by conductor 14 to the one-shot 28 which is set for a variable window interval controlled in a manner to be described and which may extend, for example, between 120 and 170 milliseconds. The output of one-shot 28 is coupled by conductor 34 to the input of one-shot 30. When one-shot 28 times out, one-shot 30 is triggered to produce an output pulse on conductor 36 which is applied through OR gate 32 to the blank input of R-wave amplifier 20. Thus, R-wave amplifier 20 is blanked or inhibited, that is rendered incapable of sensing any signal, for a short interval established by one-shot 26; then is rendered capable of sensing signals on the ventricular lead for the window period of one-shot 28; and then is again blanked for a period of time related to the normal A-V interval established by one-shot 30 (e.g. 200 ms.). In this manner, a timing window is created following the generation of an atrial pacing stimulus, during which timing window the R-wave amplifier may detect a depolarization in the ventricle. Of course, it will be understood that the R-wave amplifier 20 is not blanked for the remaining period of the atrial escape interval following the expiration of the period of the third one-shot 30. Thus the timing means establishes a blanking window established by one-shot 28 and a predetermined A-V delay interval established by one-shot 30. The normally following QRS complex would be expected to occur whether the A-V delay interval and the sense amplifier 20 would at that time be blanked. An early or late QRS complex would not be blanked. The sequence is described further in reference to FIGS. 2a and 2b.

The output of the R-wave amplifier 20 is applied through conductor 22 to one input of AND gate 40. The output of AND gate 40 is coupled through conductor 42 to one input of OR gate 44. The output of OR gate is coupled by conductor 46 to the RESET input of counter 48. The trigger pulse generated by oscillator is also coupled by conductor 50 to the COUNT input of counter 48.

AND gate 40 posseses a further input coupled by conductor 52 to the MAXIMUM rate control signal output of the decoder circuit 54. OR gate 44 has a further input coupled to the output of AND gate 56. One input of AND gate 56 is coupled via conductor 58 to the MINIMUM rate control signal output of decoder 54, and the other input is coupled via conductor 60 to the output of selector circuit 62. AND gates 40 and 56 are enabled whenever the MINIMUM and MAXIMUM rate control signals outputs of decoder 54 are low logic levels. Thus, output pulses of the selector 62 are passed through AND gate 56 and OR gate 44 to clock the UP/DOWN counter 64 as long as the decoder 54 does not generate a high logic signal on conductor 58. Similarly as long as decoder 54 has not generated a high logic signal on conductor 52, detected R-waves are passed through AND gate 40 and OR gate 44 to clock the UP/DOWN counter 64. Each time a clock input signal is passed through OR gate 44, it is also applied to conductor 46 to the RESET input of counter 48.

Counter 48 is adapted to count the number of trigger pulses produced by oscillator 10 and applied to its COUNT input terminal in the interval between CLOCK signals applied via conductor 46 to its RESET input terminal. As long as the counter 48 is RESET before it reaches a preset count (which may be remotely programmed into the selector 62), the selector 62 causes the high level UP/DOWN logic signal to be generated at its output terminal and coupled through conductor 70 to the UP/DOWN counter 64. The UP/DOWN counter 64 responds to the high level of the UP/DOWN logic signal and removes the UP count mode. However, when the count in counter 48 is not reset and reaches the preset count, the level of UP/DOWN logic signal goes low, and UP/DOWN counter 64 assumes the DOWN count mode. Over a period of time, the UP/DOWN counter count will decrease to a count at which the decoder 54 will generate the MINIMUM rate control signal. The MINIMUM rate control signal relates to the MINIMUM rate or MAXIMUM escape interval that the timing circuit of the oscillator 10 may be set at. As stated earlier when the MINIMUM rate is stored in the UP/DOWN counter 64, the AND gate 56 is inhibited, and the UP/DOWN counter 64 is no longer capable of being clocked by an output of the selector 62.

If, however, an R-wave is detected and applied through AND gate 40 and OR gate 44 to clock the UP/DOWN counter 64, the counter 48 will be simultaneously reset thus changing the logic state of the UP/DOWN logic signal on conductor 70 and causing the UP/DOWN counter 64 to start to count up.

The UP/DOWN counter 64, together with decoder 54 and D/A converter 72, establishes the escape interval or rate of the timing circuit of the oscillator 10. A count established by UP/DOWN counter 64 is decoded by decoder 54 and applied through the D/A converter 72 to a timing circuit of the oscillator 10 and cause it to either increase or decrease between the MINIMUM and MAXIMUM rates established in the decoder 54. Thus, the pacing rate or escape interval of the oscillator 10 is ordinarily at the MINIMUM rate and longest escape interval established by the decoder 54 and the UP/DOWN counter 64 at its MINIMUM count. However, when ectopic ventricular depolarizations are sensed either prior to the elapse of the escape interval of oscillator 10 or within the timing window established by timing means 16, then the sensed R-wave resets the counter 48 and clocks the UP/DOWN counter 64 to increase the count stored therein by a predetermined number. The increased count in UP/DOWN counter 64 is decoded by decoder 54 and converted by D/A converter 72 into an increased escape interval of oscillator 10, thus increasing the rate of the atrial pacing stimuli applied to the atrium. The new count in UP/DOWN counter 64 will be maintained either for a predetermined number of trigger pulses generated by oscillator 10 which are counted in counter 48 or until the next unblanked R-wave is applied to the clock input of UP/DOWN counter 64. In the former case, after the predetermined number of trigger pulses are counted in counter 48, the UP/DOWN counter is down counted back to its MINIMUM count, and the timing circuit of the oscillator 10 is restored to its preset or programmed escape interval. In the latter case, the count in UP/DOWN counter 64 is up-counted by a further predetermined number, and the escape interval is correspondingly shortened, thus increasing the atrial pacing rate. The atrial pacing rate may be increased up to the MAXIMUM rate allowed by the logic circuitry in decoder 54, whereupon the AND gate 40 is disabled and further sensed ventricular depolarizations will have no effect on the atrial pacing circuitry.

PREFERRED MODES OF OPERATION

Referring now to FIGS. 2a and 2b, there are shown the timing diagrams of the signals developed at various points in the circuit of FIG. 1, and the modes of up and down counting between the MINIMUM and MAXIMUM allowed rates of the atrial pulse generator.

Turning now to FIG. 2a there is shown in the top line an ECG tracing depicting, from left to right, a sequence of pacing artifacts produced by the atrial pulse generator (comprising the oscillator 10 and output stage 12 of FIG. 1) and QRS complexes generated by the heart. In FIG. 2a, the QRS complexes, indicated by the irregular bipolar signal, are increasing from a low to high rate, indicating that the patient has an underlying ventricular heart rhythm disassociated from the paced atrium and which is capable of increasing with the patient's physiological requirements. The pacing artifacts are indicated by the vertical lines of uniform height which correspond to the trigger pulses shown on the second line and the atrial pacing lead waveform shown at the bottom of FIG. 2a.

In reference to the second line of FIG. 2a it will be noted that the atrial pacing rate is illustratively shown to be increasing from 60 beats per minute at left up to 120 beats per minute at the right side of the figure. For purposes of illustration, it will be understood that the 60 and 120 beat per minute rates constitute the MINIMUM and MAXIMUM pacing rates of the pulse generator. Of course, the MINIMUM pacing rate may be set to any desirable pacing rate that may be programmed into the oscillator 10.

The next four lines in the waveform diagram FIG. 2a depict the response of the timing means 16 to the trigger pulses generated by oscillator 10 and the creation of the blanking window at the OR gate 32. The one-shots 26 and 28 are set by the trigger pulses generated by oscillator 10, to create the timing intervals shown on the third and fourth lines. Note that the set interval of one-shot 26 is constant at all rates depicted, whereas the set interval of one-shot 28 becomes shorter as the pacing rate increases. The constant set interval of the one-shot 30 is depicted on the fifth line. The blanking window, depicted in the seventh line constitutes the period between the termination of the set interval of the one-shot 26 and the commencement of the set interval of the one-shot 30, and becomes shorter as the pacing rate increases.

The blanking window is intended to be somewhat shorter than the A-V interval of a normal heart beating in A-V synchrony in the range from 60 to 120 beats per minute, for example. The A-V interval in a normal heart increases as the A-V synchronous heart rate increases. The blanking window is therefore selected to comprise an interval following the initial blanking of the R-wave amplifier 20 and extending to 170 milliseconds following the atrial pacing pulse at 60 beats per minute, the window interval shortening to 120 milliseconds at 120 beats per minute. The output of the D/A converter 72 is supplied to the second one-shot 28 to shorten its period as the count in UP/DOWN counter 64 increases.

As shown in FIG. 2a, the R-wave amplifier 20 is unblanked or enabled in the blanking window interval and also in the interval following the termination of the high state of one-shot 30 until the next atrial pacing stimulus is generated. In this manner, the R-wave amplifier 20 may detect QRS complexes which occur either too soon after the pacing stimulus is delivered or prior to the delivery of the pacing stimulus. In the former case, the ventricular depolarizations become disassociated from the atrial depolarizations and begin to increase in frequency achieving a rate greater than the preset rate of the atrial pacing generator. In the latter case, premature ventricular contraction (PVC) may develop which indicate that the atrial pacing rate should be increased to a rate which suppresses the PVC's.

The next line in FIG. 2a shows the UP/DOWN logic level generated by selector 62. A high logic level of the signal on conductor 70 causes the UP/DOWN counter 64 to increase its count, whereas a low logic level on conductor 70 causes the counter 64 to decrease its count (in a manner to be described) back to the MINIMUM count. The following two lines depict the signals generated at the gates 40 and 44. The next two lines show the logic levels of the MINIMUM and MAXIMUM rate control signals of the decoder 54. In general, a high logic level on either the MINIMUM or MAXIMUM output of decoder 54 inhibits or disables the associated AND gates 56 and 40 respectively, whereas the low logic level enables the respective AND gates.

Turning to the sequence of events depicted in FIG. 2a, in the first instance at the right side, the atrial pacing rate is at its MINIMUM rate of 60 beats per minute and the MINIMUM rate control signal level of decoder 54 is high thus inhibiting the AND gate 56. The UP/DOWN logic level is low, and it will be assumed that the UP/DOWN counter is at its lowest count, which when decoded by decoder 54 and D/A converter 72 establishes the escape interval of the timing circuit in oscillator 10. An atrial pacing stimulus pulse has been generated and shortly thereafter a disassociated ventricular contraction indicated by the QRS complex occurs within the blanking window. The QRS complex is sensed by the R-wave amplifier 20 and a signal passes through the gates 40 and 44 and is applied to the UP/DOWN counter 64. The clock signal is also applied to reset input of counter 48 which resets the count back to an initial count. The selector 62 responds to the new initial count in counter 48 to change the state of the UP/DOWN logic level on conductor 70. The decoder 54 responds to the new count in UP/DOWN counter 64 and switches the logic level of the MINIMUM rate control signal from high to low. Simultaneously, the D/A converter 72 responds to the decoded new count in counter 64 to shorten the escape interval of the timing circuit within oscillator 10.

Thus, the early QRS complex causes the rate of the atrial pulse generator to be increased from 60 beats per minute to 65 beats per minute, for example. Referring to the next interval depicted in FIG. 2a, the atrial pacing stimulus is generated and a QRS complex occurs within the normally expected A-V interval. Thus the QRS complex occurs outside the blanking window and within the period of the high logic level of one-shot 30. Ordinarily, if no further early or ectopic depolarizations occur, the pacing rate will remain at the 65 beat per minute, rate for a preset number of output pulses and then will revert back to the 60 bpm preset or MINIMUM rate, in a manner to be described in reference to FIG. 2b.

However, in the next example shown in FIG. 2a, a premature ventricular contraction occurs, shown by the QRS complex leading the next atrial pacing stimulus. Since that QRS complex occurs at a time when the R-wave amplifier 20 is unblanked, it responds to develop a further clock signal at the output of gate 44. That clock signal causes the count in UP/DOWN counter 64 to be increased (since the UP/DOWN logic signal on conductor 70 is high). The increased count in UP/DOWN counter 64 is decoded and converted and shortens the escape interval by a predetermined amount, resulting in a new atrial pacing rate of, for example, 70 beats per minute.

It will be assumed that the premature ventricular contractions continue to occur until the atrial pacing rate has reached 115 beats per minute as depicted in FIG. 2a. The next occurring premature ventricular contraction causes the atrial pacing rate to be increased to the MAXIMUM rate of 120 beats per minute, whereupon the decoder 54 develops the MAXIMUM rate control signal (indicated by the high logic level) which is applied via conductor 52 to AND gate 40 to inhibit or disable AND gate 40 from passing any further signals developed by R-wave amplifier 20. Thus, at 120 beats per minute, A-V synchrony is sacrificed in order to maintain the pacing rate at a safe rate. Of course, it will be understood that the upper rate limit may be programmed from time to time depending upon the needs of the patient and the ability of heart to function at higher rates to a rate above or below the 120 beats per minute. It would be expected that after a period of time the patient's physiological requirements would decrease, and that A-V synchrony would be restored at some rate below the MAXIMUM rate.

The pacemaker as described above behaves like a phase locked loop oscillator by bringing the atrium into the desired phase by stimulation upon sensing ventricular activity exceeding in rate the rate of the atrial pulse generator. Hence, the shortened escape intervals of the ventricular depolarizations shown on the second line of FIG. 2a are out of phase with the atrial pacing pulse escape intervals and the circuit adjusts the atrial pacing rate accordingly.

In a further mode of operation, the circuit and method of the present invention operates to treat atrial tachycardias. Let us assume the stable heart rate of 80 BPM and atrial pacing at the same rate. If now the intrinsic rate of the normal heart increases to 82 BPM, the circuit in each one would then go back into phase and stimulate the heart with a frequency one step higher, e.g. 85 BPM. If the heart rate goes to 87 BPM, the circuit would step up to 90 BPM and wait again. The circuit would get into phase with the heart within one stepping-up cycle and then would wait for the ventricular rate to increase or decrease.

Unlike the gradual increase of physiologic tachycardia, the onset of pathologic tachycardia is sudden. Let us presume that the heart rate is 70 BPM and that suddenly, the frequency of the heart rises to 120 BPM. The difference is 50 BPM. The VSAP now would need 10 consecutive steps to get into phase, as with one step, it can only cover a range of e.g. 5 BPM rate rise. If such a sudden tachycardia develops, the circuit continues stimulation with increasing rate, as basically, it cannot be inhibited. The stimuli would hit the heart at various coupling intervals and thereby may break the tachycardia.

The number of steps to be taken consecutively to go back into phase can give the information upon the tachycardia frequency; the fact that consecutive steps are necessary tells that pathologic tachycardia is present, irrespective of its actual frequency.

The manner in which the circuit of FIG. 1 accomplishes the decrease in the atrial pacing rate back to the MINIMUM or preset rate is shown in FIG. 2b. In FIG. 2b, it will be assumed that the atrial pacing rate has been increased to a rate of 70 beats per minute, for example, in the manner described in reference to FIG. 2a. Each trigger pulse generated by oscillator 10 is counted by counter 48. As long as counter 48 is not reset by a clock signal resulting from a sensed R-wave, the count in counter 48 increases until it reaches a predetermined count (3 in the example shown). At that point, the selector 62 generates a signal which is applied via conductor 60 to the other input of AND gate 56 which passes that signal through OR gate 44 to the UP/DOWN counter 64. That clock signal is applied via conductor 46 back to the RESET input of counter 48 to reestablish the initial count. Simultaneously, the clock signal is applied to the UP/DOWN counter 64 which responds by reducing its count by a predetermined number. The UP/DOWN counter 64 is in the DOWN count mode inasmuch as the UP/DOWN logic level signal is low. The new count in UP/DOWN counter 64 is decoded and converted and increases the escape interval of the timing means in oscillator 10. The resulting rate of the atrial pulse generator is shown, for example, 65 beats per minute. The same sequence of events recurs, absent any disassociated or ectopic QRS complexes or episodes of tachycardia for a further predetermined interval resulting again in the reduction in the count stored in the UP/DOWN counter 64. When that count reaches the count corresponding to the MINIMUM rate or preset pacing escape interval, the decoder 54 responds by producing the high logic level MINIMUM signal which then inhibits AND gate 56 and prevent the generation of further clock signals when the count in counter 58 reaches the predetermined number. The pulse generator stays at the MINIMUM rate as long as the A-V synchrony is maintained.

In the tachycardia treatment mode, when the tachycardia is broken, the circuit will at once go into phase with the heart and there will be no further rate increase. But the circuit will still stimulate the heart at the frequency with which it was possible to break the tachycardia. This stimulation of the atria at an elevated frequency is a valuable therapeutic tool in post-tachycardia stabilization of the rhythm. Then, as the circuit gradually decreases the atrial pacing rate in the manner described in reference to FIG. 2b, the heart may slowly stabilize to the initial lower rate.

The various rates and intervals employed to illustrate the principles of the invention may be altered as desired. For example, the selector 62 may be programmed to respond to any predetermined count in counter 48. Similarly, the decoder 54 and D/A converter 72 may be designed to convert the count in UP/DOWN counter 64 into any predetermined change in the escape interval of the timing means of oscillator 10. The time intervals selected for the first, second, and third one-shots 26, 28 and 30 may similarly be adjusted as desired. Although decimal numbers are employed in the illustration of the invention to specify the intervals and the counts, it will be understood that the invention may be implemented in digital logic circuitry which would dictate the use of binary counting systems resulting in pacing rates and intervals which may not be the exact numerals shown in the examples. The counters, selectors, decoders, D/A converter and oscillator may all be selected from known digital storage and logic circuits in a manner known to those skilled in the art.

Thus, the ventricular synchronized atrial pacemaker shown and described above may advantageously maintain or seek to maintain A-V pacing synchrony over a wide range of atrial pacing rates. The atrial pacing rate may be increased or decreased as the detected ventricular rate indicates. The circuitry shown may be implemented into a pacing system of any of the types hereinbefore described. The simplicity of the circuitry may make it easily implemented into fully programmable dual demand pacemakers already possessing the requisite capability for atrial and ventricular lead connections and the atrial oscillator and output stage and R-wave amplifier.

Having thus described our invention with particularity in reference to preferred form, it will be obvious to those skilled in the art, after understanding our invention, that other changes and modifications may be made to it without departing from the spirit and scope of the invention, and we intend the appended claims to cover such changes and modifications as are within the scope of the invention.

What we claim is:

1. A synchronous heart pacemaker comprising:
   atrial pacing pulse generator means for generating stimulating pulses adapted to be applied to the atrium at an atrial pacing rate;
   means for sensing ventricular heart depolarizations;
   means for timing the interval between atrial pacing pulses and ventricular depolarizations and for producing a clock signal when ventricular depolarizations occur out of synchronism with atrial pacing pulses; and
   atrial pacing rate adjusting means responsive to the clock signal for adjusting the atrial pacing rate to restore synchrony.

2. The heart pacemaker of claim 1 wherein said sensing means comprises a ventricular sense amplifier having first input means adapted to be coupled to the ventricle of the heart to receive electrical signals in the ventricle, amplifier means for amplifying and shaping sensed electrical signals and producing an output signal, and second input means adapted to respond to said timing means for inhibiting the production of said output signal when the ventricular depolarizations occur in synchrony with atrial pacing pulses.

3. The heart pacemaker of claim 2 wherein said timing means comprises:
   blanking window signal generating means responsive to the generation of atrial stimulating pulses for producing a first blanking signal for a first predetermined interval for preventing the response of said ventricular sense amplifier means to the generated atrial stimulating pulse and a second blanking signal over a subsequent interval for preventing the response of said sense amplifier means to ventricular depolarizations triggered by the preceding atrial stimulating pulse; and
   means for applying the first and second blanking signals to said second input means.

4. The heart pacemaker of claim 3 wherein said blanking window generating means further comprises means responsive to the generation of the atrial stimulating pulses for separating the first and second intervals by a third interval representative of a physiological atrial-ventricular delay interval and means responsive to the atrial pacing rate for adjusting the third interval in proportion to the rate.

5. The heart pacemaker of claim 4, wherein said blanking window signal generating means further comprises:
- a first one-shot set by the generation of the atrial stimulating pulse for the first interval;
- a second one-shot set by the generating of the atrial stimulating pulse for the third interval;
- a third one-shot set at the reset of the second one-shot for the second interval; and
- gate means for coupling the set states of the first and third one-shots to said second input means of said ventricular sense amplifier.

6. The heart pacemaker of claim 1 wherein said atrial pacing rate adjusting means further comprises rate counter means for storing a rate count and wherein said atrial pacing pulse generator means is responsive to the rate count stored in said rate counter means for establishing the atrial pacing rate.

7. The heart pacemaker of claim 6 wherein said atrial pacing rate adjusting means further comprises:
- means for increasing the atrial pacing rate in response to a clock signal.

8. The heart pacemaker of claim 7 wherein said means for increasing the atrial pacing rate further comprises:
- first counter means responsive to a clock signal for producing an up count signal; and
- said rate counter means is responsive to the clock signal and the up count signal for increasing a higher atrial pacing rate.

9. The heart pacemaker of claim 8 wherein said atrial pacing rate adjusting means further comprises means for decreasing an increased atrial pacing rate wherein:
- said first counter means is responsive to the generation of an atrial pacing pulse for counting the number of atrial pacing pulses generated between clock signals; and
- said first counter means is responsive to the clock signal for resetting the count;
- and wherein said first counter means further comprises:
- selector means responsive to a certain count in said first counter means for generating a down count signal; and wherein
- said rate counter means is responsive to the clock signal and the down count signal for decreasing the rate count from a higher count to a lower count for establishing a lower atrial pacing rate.

10. The heart pacemaker of claim 9 wherein said selector means is responsive to the certain count of said first counting means for producing an output signal and further comprising:
- logic means responsive to said output signal for producing a clock signal, and
- wherein said first counter means is responsive to said clock signal for resetting the count in said first counter means to its initial count.

11. The heart pacemaker of claim 6 or 10 wherein said rate counter means further comprises:
- decoder means responsive to the rate count for producing maximum and minimum rate control signals when the rate count reaches counts which establish maximum and minimum atrial pacing rates.

12. The heart pacemaker of claim 11 wherein said logic means is responsive to said maximum and minimum rate control signals for inhibiting the production of clock signals in response to the ventricular sense amplifier means and the selector means, respectively.

13. The heart pacemaker of claim 6 wherein said sensing means comprises a ventricular sense amplifier having first input means adapted to be coupled to the ventricle of the heart to receive electrical signals in the ventricle, amplifier means for amplifying and shaping sensed electrical signals and producing an output signal, and second input means adapted to respond to said timing means for inhibiting the production of said output signal when the ventricular depolarizations occur in synchrony with atrial pacing pulses.

14. The heart pacemaker of claim 13 wherein said timing means comprises:
- blanking window signal generating means responsive to the generation of atrial stimulating pulses for producing a first blanking signal for a first predetermined interval for preventing the response of said ventricular sense amplifier means to the generated atrial stimulating pulse and a second blanking signal over a subsequent interval for preventing the response of said sense amplifier means to ventricular depolarizations triggered by the preceding atrial stimulating pulse; and
- means for apply the first and second blanking signals to said second input means.

15. The heart pacemaker of claim 14 wherein said blanking window generating means further comprises means responsive to the generation of the atrial stimulating pulses for separating the first and second intervals by a third interval representative of a physiological atrial-ventricular delay interval and means responsive to the atrial pacing rate for adjusting the third interval in proportion to the rate.

16. The heart pacemaker of claim 15, wherein said blanking window signal generating means further comprises:
- a first one-shot set by the generation of the atrial stimulating pulse for the first interval;
- a second one-shot set by the generating of the atrial stimulating pulse for the third interval;
- a third one-shot set at the reset of the second one shot for the second interval; and
- gate means for coupling the set states of the first and third one shots to said second input means of said ventricular sense amplifier.

17. A method of synchronous heart pacing comprising the steps of:
- generating atrial pacing stimulating pulses adapted to be applied to the atrium at an atrial pacing rate;
- sensing ventricular heart depolarizations;
- timing the interval between atrial pacing pulses and ventricular depolarizations; and
- adjusting the atrial pacing rate when the ventricular depolarizations do not fall within a predetermined atrial-ventricular delay interval following an atrial pacing pulse.

18. The method of claim 17 wherein said step of adjusting the atrial rate further comprises:
- increasing the atrial pacing rate when ventricular depolarizations are sensed before the predetermined atrial-ventricular delay interval.

19. The method of claim 17 wherein said step of adjusting the atrial rate further comprises:

increasing the atrial pacing rate when ventricular depolarizations are sensed after the predetermined atrial-ventricular delay interval.

20. The method of claim 18 or 19 further comprising the step of:

preventing the atrial pacing rate from exceeding a maximum atrial pacing rate.

21. The method of claim 17 further comprising the step of:

returning the atrial pacing rate to its preset rate for an increased rate when subsequent ventricular depolarizations fall in the atrial-ventricular delay interval.

22. The method of claim 17 further comprising the steps of:

counting atrial pacing pulses;

producing a clock signal when ventricular depolarizations are sensed at a time outside the predetermined atrial-ventricular delay window; and wherein said step of adjusting the atrial pacing rate further comprises the step of:

decreasing the atrial pacing rate when a predetermined number of atrial pacing pulses are counted following the last clock signal.

23. The method of claim 22 wherein said step of adjusting the atrial pacing rate further comprises the step of:

increasing the atrial pacing rate in response to a clock signal.

24. The method of claim 22 or 23 further comprising the step of:

preventing the atrial pacing rate from exceeding a maximum pacing rate.

25. The method of claim 22 further comprising the step of:

preventing the decrease of the atrial pacing rate below a minimum pacing rate.

\* \* \* \* \*

UNITED STATES PATENT AND TRADEMARK OFFICE
CERTIFICATE OF CORRECTION

PATENT NO. : 4,284,082

DATED : August 18, 1981

INVENTOR(S) : FUNKE et al

It is certified that error appears in the above-identified patent and that said Letters Patent are hereby corrected as shown below:

Claim 8,
　　Line 34, after "increasing" insert --the rate count to a higher count for establishing--

Signed and Sealed this

Nineteenth Day of January 1982

[SEAL]

Attest:

GERALD J. MOSSINGHOFF

Attesting Officer　　Commissioner of Patents and Trademarks